(12) United States Patent
Martens et al.

(10) Patent No.: US 8,818,490 B2
(45) Date of Patent: Aug. 26, 2014

(54) INSTRUMENT GUIDING DURING MAGNETIC RESONANCE IMAGING

(75) Inventors: Hubert Cecile Francois Martens, Eindhoven (NL); Judith Margeet Rensen, Veldhoven (NL); Michel Marcel Jose Decre, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 26 days.

(21) Appl. No.: 13/640,517

(22) PCT Filed: Mar. 31, 2011

(86) PCT No.: PCT/IB2011/051384
§ 371 (c)(1),
(2), (4) Date: Oct. 11, 2012

(87) PCT Pub. No.: WO2011/128800
PCT Pub. Date: Oct. 20, 2011

(65) Prior Publication Data
US 2013/0035585 A1  Feb. 7, 2013

(30) Foreign Application Priority Data
Apr. 14, 2010  (EP) .................................... 10159885

(51) Int. Cl.
*A61B 5/055*  (2006.01)
(52) U.S. Cl.
USPC ............................ 600/411; 600/417; 600/422
(58) Field of Classification Search
USPC ......... 600/410, 411, 417, 421, 422, 424, 425, 600/429; 606/54, 56, 130; 324/318
See application file for complete search history.

(56) References Cited

U.S. PATENT DOCUMENTS

| 5,706,812 | A | 1/1998 | Strenk et al. |
| 6,529,764 | B1 * | 3/2003 | Kato et al. ................... 600/411 |
| 7,313,430 | B2 | 12/2007 | Urquhart et al. |
| 2009/0069811 | A1 | 3/2009 | Lindfors et al. |
| 2009/0079431 | A1 | 3/2009 | Piferi et al. |
| 2009/0112082 | A1 | 4/2009 | Piferl et al. |

FOREIGN PATENT DOCUMENTS

| EP | 1090594 A1 | 4/2001 |
| EP | 1264577 A1 | 12/2002 |
| GB | 2370778 A | 7/2002 |
| JP | 9094233 A | 9/1995 |
| JP | 2006015045 A | 1/2006 |

OTHER PUBLICATIONS

Nicky H.G.M. Peters, Carla Meeuwis, Chris J.G. Bakker, Willem P.TH.M. Mali, Arancha M. Fernandez-Gallardo, Richard Van Hillegersberg, Margerite E. I. Schipper, Maurice A.A.J. Van Den Bosch. European Radiology, vol. 1, Jul. 19, 2009 (7) 1639-1644.

* cited by examiner

*Primary Examiner* — Michael Rozanski (57) ABSTRACT

The invention relates to a preparing apparatus for preparing an influencing procedure for influencing a subject. The preparing apparatus (1) comprises a subject coil (3) for generating a magnetic resonance image of he subject (7), an instrument guide device (5) for guiding an instrument (6) for influencing the subject (7), a marker (9) being visible in the magnetic resonance image, and an attaching element for attaching the instrument guide device (5) to the subject coil (3) in a known spatial relationship. Since the spatial relationship between the instrument guide device (5) and the subject coil (3) is known, if they are attached to each other, a time consuming registration procedure for registering an influence trajectory, which has been planned based on the magnetic resonance image, and the instrument guide device (5) can be avoided.

8 Claims, 6 Drawing Sheets

INSTRUMENT GUIDING DURING MAGNETIC RESONANCE IMAGING

FIELD OF THE INVENTION

The invention relates to a preparing apparatus and preparing method for preparing an influencing procedure for influencing a subject. The invention relates further to a subject coil and an instrument guide device, which are adapted to be cooperated with each other for preparing an influencing procedure for influencing a subject. The invention relates also to a magnetic resonance imaging system for imaging a subject.

BACKGROUND OF THE INVENTION

EP 1 090 594 A1 discloses a system for performing a surgical operation, wherein the system comprises a coil body forming a loop adapted to surround an object to be imaged and a puncture needle support tool engaged with the coil body. The puncture needle support tool comprises a first base member having means for attachment to a radiofrequency coil, a second base member attached to the first base member movably in a direction substantially parallel to the axis of the radiofrequency coil, and a guide member comprising a puncture needle passage and a magnetic resonance marker disposed along the puncture needle passage. The guide member is attached to the second base member movably in a direction substantially perpendicular to the axis of the radiofrequency coil and rotatably in a plane substantially perpendicular to the axis of the radiofrequency coil.

The article "Feasibility of MRI-guided large-core-needle biopsy of suspicious breast lesions at 3T" by N.H.G.M. Peters et al., European Radiology, volume 19, pages 1639 to 1644 (2009) discloses a system for performing a magnetic resonance guided breast biopsy. The system consists of a breast coil and an add-on stereotactic biopsy system. The stereotactic biopsy system comprises a gadolinium-filled guiding marker tube.

US 2009/0112082 A1 discloses a head support apparatus for engaging and securing the head of a patient, and a targeting frame configured to be secured to the head of the patient. The targeting frame includes a cooperating targeting cannula that is configured to guide placement of an interventional device through a burr hole in a patient's skull in vivo. Moreover, the targeting frame comprises fiducial markers being visible in a magnetic resonance (MR) image. The head support apparatus and the targeting frame are separate elements. The time needed for preparing an interventional procedure by using the head support apparatus and the targeting frame is quite long.

SUMMARY OF THE INVENTION

It is an object of the present invention to provide a preparing apparatus for preparing an influencing procedure for influencing a subject, wherein the time needed for preparing the influencing procedure can be reduced.

In a first aspect of the present invention a preparing apparatus for preparing an influencing procedure for influencing a subject is presented, wherein the preparing apparatus comprises
a subject coil for generating a magnetic resonance image of the subject,
an instrument guide device for guiding an instrument for influencing the subject,
a marker being visible in the magnetic resonance image,
an attaching element for attaching the instrument guide device to the subject coil in a known spatial relationship.

Since the spatial relationship between the instrument guide device and the subject coil is known, if they are attached to each other, a time consuming registration procedure for registering an influence trajectory, which has been planned based on the MR image, and the instrument guide device can be avoided. In particular, coordinates of an influencing trajectory in an instrument guide coordinate system in which the instrument guide device should guide the instrument, preferentially stereotactic coordinates in a stereotactic coordinate system if the influencing procedure is a stereotactic procedure, are readily determinable from the spatial position of a planned influencing trajectory in an MR image space, the spatial position of the marker in the MR image, i.e. in the MR image space, the spatial position of the marker in the instrument guide coordinate system, and the known spatial relationship between the subject coil and the instrument guide device.

In contrast, in the above mentioned prior art, the head support apparatus and the targeting frame are separate elements with an a priori unknown spatial relationship. Registration procedures for registering the MR image with the targeting frame are therefore needed, in order to allow the targeting cannula to guide the placement of the interventional device in accordance with a planned trajectory. This requires additional effort and is time consuming. Thus, in the prior art, the time for preparing such an interventional procedure is quite long.

The instrument guide device is preferentially integrated in the subject coil.

The subject coil is preferentially a radiofrequency (RF) coil.

The subject is preferentially a head of a person, wherein the subject coil is preferentially adapted to generate a magnetic resonance image of the head, and the instrument guide device is preferentially adapted to guide an instrument for influencing the head. In particular, the subject coil is preferentially an RF head coil having the marker which is preferentially an integrated stereotactic fiducial being visible in the magnetic resonance image.

The preparing apparatus is preferentially adapted to prepare a stereotactic surgical procedure, in particular, which shall be applied to the head of a person. The preparing apparatus is preferentially further adapted to perform the prepared stereotactic surgical procedure.

The attaching element is preferentially adapted to attach the instrument guide device and the subject coil to each other in a detachable way. For example, the attaching element can be formed by a receiving element on the subject coil and a corresponding fitting element on the instrument guide device, which is adapted to be fitted into the receiving element, or vice versa. If the marker is arranged at the subject coil, it is possible to completely prepare the influencing procedure, without attaching the instrument guide device to the subject coil, wherein, if the instrument guide device is finally attached to the subject coil, the instrument guide device is already registered because of the known spatial relationship between the instrument guide device and the subject coil. Thus, during preparation of the influencing procedure an easier access to the subject can be provided, without additional registration procedures, after the instrument guide device has finally been attached to the subject coil. Moreover, since the instrument guide device and the subject coil can be attached to each other in a detachable way, the instrument guide device can be used with different subject coils and the subject coil can be used with different instrument guide devices.

The preparing apparatus can comprise one or several markers, which are located at known spatial positions with respect to the subject coil.

It is preferred that the instrument guide device comprises an instrument holder for holding the instrument and an instrument holder carrier for carrying the instrument holder, wherein the attaching element is adapted to attach the subject coil and the instrument holder carrier to each other such that the instrument guide device and the subject coil are in a known spatial relationship. For example, a receiving element can be provided on the subject coil, which is adapted to receive the instrument holder carrier, for forming the attaching element. The instrument holder carrier is preferentially a plate, in particular, an endplate for being attached to an end of the subject coil. Preferentially, the endplate can be easily fitted on the subject coil in a unique and mechanically robust manner. The marker can also be provided on the instrument holder carrier.

The instrument guide device is adapted to allow the instrument to be moved with respect to the subject coil, for example, in order to move the instrument along a desired trajectory. For example, the instrument guide device can be adapted to move an interventional instrument into the skull of a person or into another subject.

It is further preferred that the instrument holder and the instrument holder carrier are adapted to allow the instrument holder to be moved with respect to the instrument holder carrier for moving the instrument with respect to the subject coil.

Preferentially, the instrument holder carrier is a plate, in particular, an endplate, and the plate and the instrument holder are adapted to allow the instrument holder to be translated in the plane of the plate. It is further preferred that the instrument guide device is adapted to allow the instrument holder, in particular, a part of the instrument holder, to be rotated with respect to the instrument holder carrier. For example, the instrument holder can comprise an outer part and an inner part, which is rotatable with respect to the outer part and which directly holds the instrument, in order to allow the instrument to be rotated with respect to the subject coil, in particular, with respect to the subject. This enables a variety of trajectories of the instrument within the subject coil, in particular, within the subject.

It is further preferred that the marker is attached to at least one of the subject coil and the instrument guide device. In particular, the marker is arranged within the subject coil. Preferentially, the marker is rigidly fixed to the interior of the subject coil. This ensures that the marker is well within the imaging field of the subject coil and close to the subject.

The preparing apparatus preferentially further comprises a subject holding structure for holding the subject. It is preferred that the subject coil is arranged within the subject holding structure. This further ensures that the subject coil can be located close to the subject, wherein the subject is placed within the subject coil. The subject coil preferentially comprises holding openings and the subject holding structure comprising corresponding holding elements for penetrating the holding openings for holding the subject within the subject coil in place.

The subject holding structure is preferentially adapted to fix the subject in a desired position. The subject holding structure preferentially comprises a clamping construction to clamp the subject in a fixed position within the subject coil. The subject holding structure can be adaptable in shape to accommodate a subject-specific shape, in particular, a patient-specific anatomy, and is preferentially adapted to hold a head of a person in place.

The attaching element can be adapted to attach the instrument guide device to the subject coil directly or via another element, i.e. indirectly. For example, the instrument guide device and the subject coil can be directly attached together or, for example, via the subject holding structure or another element such that the spatial relationship between the instrument guide device and the subject coil is known. The instrument guide device is configured such that the spatial relationship between an instrument guided by the instrument guide device and the subject coil is known, if the spatial relationship between the instrument guide device and the subject coil is known.

The preparing apparatus can comprise an opening generating unit for generating an opening in the subject for allowing the instrument guide device to guide the instrument into the subject. For example, the instrument holder carrier, in particular, the endplate, can be equipped with a drilling unit for drilling an opening into the subject, while the instrument holder carrier is attached to the subject coil.

It is further preferred that the subject holding structure comprises more deformable regions and less deformable regions, wherein the subject coil is attached to the subject holding structure at the less deformable regions of the subject holding structure. This reduces possible influences of holding the subject, in particular, of clamping the subject, by the subject holding structure on the spatial relationship between the instrument guide device and the subject coil. For example, a possible transfer of a deformation of the subject holding structure to the subject coil can be reduced. The accuracy of preparing an influencing procedure for influencing a subject can therefore be increased.

In a further aspect of the present invention a magnetic resonance imaging system for imaging a subject is presented, wherein the magnetic resonance imaging system is adapted to generate a magnetic resonance image of the subject by using magnetic resonance signals from the subject coil of the preparing apparatus defined in claim 1.

In a further aspect of the present invention a subject coil for cooperating with an instrument guide device for guiding an instrument for influencing a subject is presented, wherein the subject coil is adapted to generate a magnetic resonance image of the subject and comprises an attaching element for attaching the instrument guide device to the subject coil in a known spatial relationship. The subject coil preferentially further comprises a marker being visible in the magnetic resonance image.

In a further aspect of the present invention an instrument guide device for cooperating with a subject coil is presented, wherein the instrument guide device is adapted to guide an instrument for influencing a subject and comprises an attaching element for attaching the instrument guide device to the subject coil in a known spatial relationship, the subject coil is adapted for generating a magnetic resonance image of the subject. The instrument guide device preferentially further comprises a marker being visible in the magnetic resonance image.

In a further aspect of the present invention a preparing method for preparing an influencing procedure for influencing a subject is presented, wherein the preparing method is adapted to use the preparing apparatus as defined in claim 1 and comprises:

generating a magnetic resonance image of the subject and of the marker by using the subject coil, determining an influence location, at which the subject should be influenced, based on a provided influence location image region, which represents the influence location, within the generated magnetic resonance image, the generated magnetic resonance image, the position of the marker and the known spatial relationship between the instrument guide device and the subject coil, which will be present during influencing the subject, attaching the instrument guide device to the subject coil by the attaching element for guiding the instrument by the instrument guide device in accordance with the determined influence location for influencing the subject.

The influence location is preferentially an influence trajectory, in particular, a surgical trajectory. The trajectory is preferentially determined in stereotactic coordinates that provide lateral and vertical positions and preferentially an angular orientation of the instrument holder.

The sequence of the steps can be modified. For example, the influence location can be determined after the instrument guide device has been attached to the subject coil. Moreover, the step of attaching the instrument guide device to the subject coil can be performed before generating the magnetic resonance image, in particular, before positioning the subject, particularly if the instrument guide device comprises markers being visible in the magnetic resonance image. The method can further comprise the step of positioning the subject within the subject holding structure of the subject coil, in particular, before generating the magnetic resonance image.

The influence location image region can be provided by a person and/or can automatically be provided, wherein, for example a target location and a trajectory from the target location to the outside can be defined. For example, a trajectory from the target location to the outside can be determined in such a way that minimal neurological damage is inflicted, for example, by avoiding large blood vessels along the trajectory and by preventing trans-ventricular and trans-sulcal trajectories. The selection and optimization of trajectories can be done by visual inspection of candidate trajectories in the context of magnetic resonance images. Preferentially, three-dimensional magnetic resonance images are reformatted along planes that are oriented along selected candidate trajectories, in order to have an optimal assessment of the respective trajectory. If the influence location image region, which represents the influence location, within the generated magnetic resonance image has been provided, the influence location with respect to a coordinate system, in which the instrument guide device moves the instrument guide, in particular, with respect to a stereotactic coordinate system, can be determined based on the position of the marker within the generated magnetic resonance image, the position of the marker with respect to this coordinate system and the known spatial relationship between the instrument guide device and the subject coil with simple geometrical considerations.

It shall be understood that the preparing apparatus of claim 1, the magnetic resonance imaging system of claim 9, the subject coil of claim 10, the instrument guide device of claim 11, and the preparing method of claim 12 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF EMBODIMENTS

Figure 1:
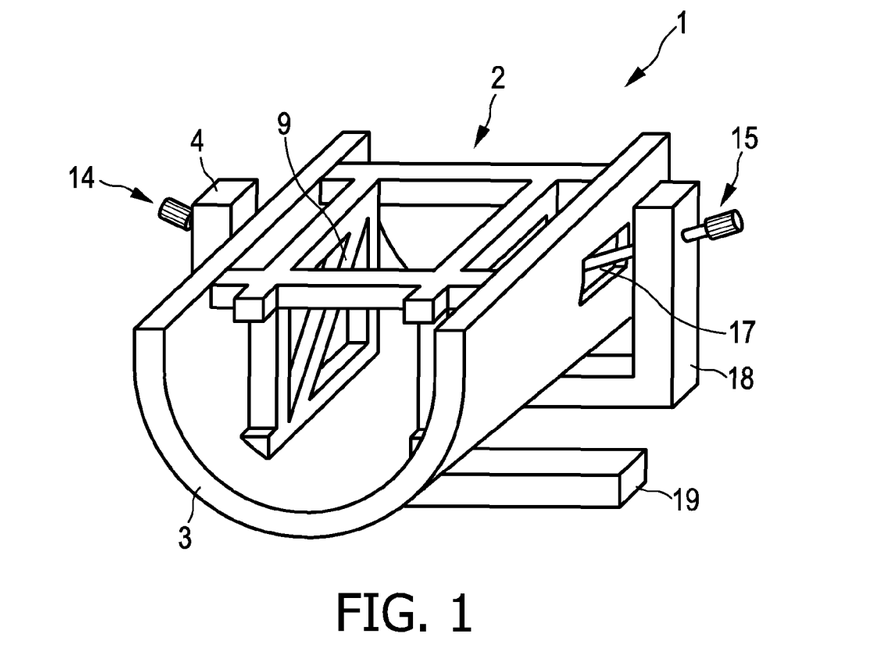
FIGS. 1 to 3 show schematically and exemplarily an embodiment of a preparing apparatus for preparing an influencing procedure for influencing a subject.

FIG. 1 shows schematically and exemplarily a preparing apparatus 1 for preparing an influencing procedure for influencing a subject in a cut view. The preparing apparatus 1 comprises a subject coil 3 for generating a magnetic resonance image of the subject and a subject holding structure 4 for holding the subject. The preparing apparatus further comprises a structure 2 with markers 9 being visible in the magnetic resonance image and arranged within the subject coil 3. The structure 2 comprises several bars, wherein Z-shaped bars 9 are located in two parallel planes and are filled with contrast fluid being visible in the magnetic resonance image. These Z-shaped markers 9 allow a very easy derivation of the stereotactic z coordinate, i.e. of the stereotactic coordinate along the main axis of the subject coil, from the height of the dots representing the diagonal element of the Z-shaped markers 9 on an axial magnetic resonance image with respect to the dots representing the horizontal elements of the markers 9. In other embodiments, other markers having other shapes can be used. For example, active markers can be used instead of image contrast providing markers, which may lead to higher accuracy.

In this embodiment, the preparing apparatus 1 is adapted to prepare a stereotactic brain surgery, i.e. the subject is a head of a person, wherein the subject coil 3 is a RF head coil and the subject holding structure 4 is adapted to stereotacticly hold the head in place. The RF head coil 3 is adapted to generate a magnetic resonance image of the head and of the markers 9 being preferentially integrated stereotactic fiducials which are visible in the magnetic resonance image. The markers 9 are rigidly fixed to the interior of the RF head coil 3, in order to ensure that the markers 9 are well within the imaging field of the RF head coil 3, close to the head and at a known spatial position.

The subject holding structure 4 is adapted to provide a clamping construction for clamping the head in a fixed position within the RF head coil 3. In particular, the subject holding structure 4 comprises holding elements being head clamping rods 14, 15 which are arranged such that they can penetrate holding openings 17 in the RF head coil 3 for holding the head within the RF head coil 3 in place. The holding elements 14, 15 are supported by a supporting structure 18 in which the RF head coil 3 is located, wherein the supporting structure 18 encloses a part of the RF head coil 3 such that the supporting structure 18 also supports the RF head coil 3. In addition the RF head coil is arranged on and supported by a coil support 19. The supporting structure 18 is preferentially U-shaped. However, in other embodiments the supporting structure can have another shape, for example, an additional bar can be provided on the top of the supporting structure such that the supporting structure has an O-shape. The additional bar can provide more rigidity.

The subject coil is preferentially attachable to a magnetic resonance imaging system directly or indirectly, for example, via the supporting structure 18 or the coil support 19. In this embodiment, the attachment between the subject coil and the magnetic resonance imaging system does not have to be rigid, because the registration of stereotactic coordinates relies on the visualization of the markers and the known spatial relationship between the subject coil and the instrument guide device and, in contrast to the prior art procedure, a perfect realignment in magnetic resonance image coordinates is not necessary.

Since FIG. 1 shows a cut view of the preparing apparatus 1, the subject coil seems to have a semi-cylindrical shape. However, in this embodiment, the subject coil 3 is preferentially cylindrically shaped. But, the subject coil can also have another shape being suitable for generating magnetic resonance images of the subject. Concerning the structure 2 with the markers 9 and the subject holding structure 4 parts of these structures are not cut away in FIG. 1.

Figure 2:
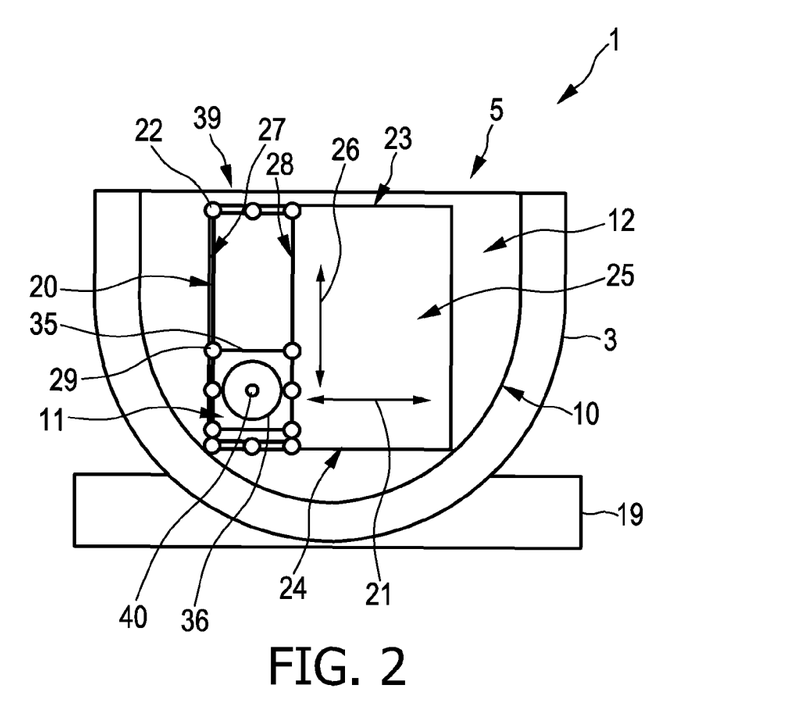

The preparing apparatus 1 further comprises an instrument guide device 5 for guiding an instrument for influencing the subject 7, which can be attached to the subject coil 3 by an attaching element 10 in a known spatial relationship. In FIG. 1, the preparing apparatus 1 is shown, before the instrument guide device 5 is attached to the subject coil 3. In FIG. 2, which schematically and exemplarily shows a back view of the preparing apparatus 1, the instrument guide device 5 is shown being attached to the subject coil 3 by the attaching element 10. In this embodiment, the instrument guide device 5 is adapted to guide a surgical instrument for performing a brain surgery. The attaching element 10 is adapted to attach the instrument guide device 5 and the subject coil 3 to each other in a detachable way. In this embodiment, the attaching element 10 is formed by a recess in the inner surface of the RF head coil 3 being a receiving element on the subject coil 3 for receiving an instrument holder carrier being an endplate 12. The instrument guide device 5 comprises an instrument holder 11 for holding the instrument and the instrument holder carrier being the endplate 12 for carrying the instrument holder 11. The endplate 12 can be easily fitted on the RF head coil 3 in a unique and mechanically robust manner.

The instrument guide device 5 is adapted to allow a user and/or an automatic moving unit to move the instrument with respect to the subject coil 3, in order to move the instrument along a desired trajectory within the subject, in particular, within the head. In this embodiment, the instrument holder 11 and the instrument holder carrier 12 are adapted to allow a user and/or an automatic moving unit to move the instrument holder 11 with respect to the instrument holder carrier 12, i.e. with respect to the endplate 12, for moving the instrument with respect to the subject coil 3. The endplate 12 and the instrument holder 11 are adapted to allow the instrument holder to be translated in the plane of the endplate 12. The instrument guide device 5 is further adapted to allow the instrument holder 11 or a part of the instrument holder 11 to be rotated with respect to the endplate 12. This enables a variety of trajectories of the instrument within the subject coil 3, in particular, within the head.

In this embodiment, the preparing apparatus comprises a sliding arrangement 39 for translating the instrument holder 11 within an opening 25 provided in the endplate 12 in horizontal and vertical directions. A sliding frame 20 is provided, which is adapted to slide on sliding rails 23, 24 in horizontal directions 21. The sliding frame 20 can comprise rolls 22 for rolling and/or sliding on sliding rails 23, 24 provided on the horizontal sides of the opening 25 within the endplate 12. Within this sliding frame 20 the instrument holder 11 can slide in vertical directions 26 along vertical sliding rails 27, 28. Also the instrument holder 11 can comprise sliding rolls 29 for sliding and/or rolling on the vertical sliding rails 27, 28.

Please note that, for clarity reasons, FIG. 2 does only show some elements of the preparation apparatus 1, in particular, the elements needed for explaining the movement of the instrument holder within the opening 25 in the endplate 12.

The instrument holder 11 is preferentially adapted to allow an instrument being held by the instrument holder to be rotated and tilted with respect to the endplate 12. For example, the instrument holder can comprise an outer part 35 and an inner part 36, which is rotatable and/or tiltable with respect to the outer part 35. The rotatable inner part 36 can be fixed at a desired rotational position and/or tilted position with respect to the outer part 35 by using a fixation element like a fixation screw. The rotatable inner part 36 can be rounded and can comprise a cylindrical receiving element 40 for receiving the instrument. The instrument holder can be constructed, for example, as shown in FIGS. 1 to 3 of DE 198 08 220 A1, which are herewith incorporated by reference.

Figure 3:
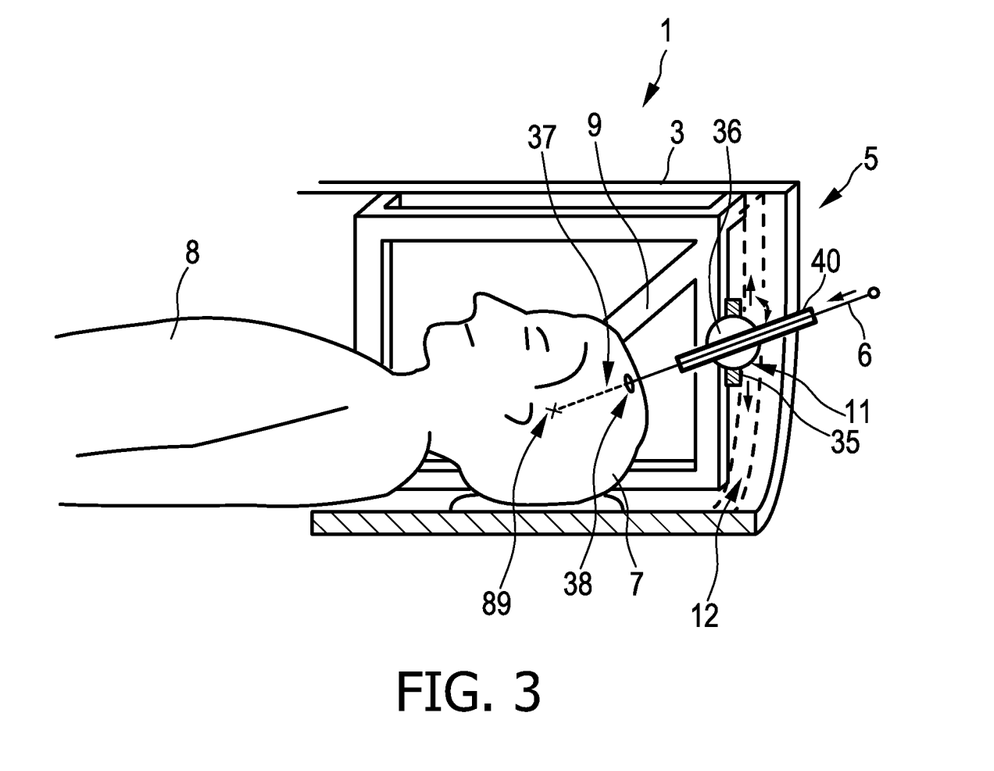

FIG. 3 shows schematically and exemplarily some elements of the preparing apparatus 1 in a partly cross-sectional view. In FIG. 3, a person 8 with a head 7 has been located within the RF head coil 3. An opening 38 has been drilled in the skull of the head 7 and an instrument 6, in this embodiment, a brain surgery instrument 6, is held within the instrument holder 11 carried on the endplate 12 which is indicated by broken lines in FIG. 3. The instrument 6 can be moved and guided along the trajectory 37 to the target location 89. It should be noted that FIG. 3 only shows some elements and particularly only parts of some elements of the preparing apparatus 1. For example, FIG. 3 only shows a part of the markers 9.

Figure 4:
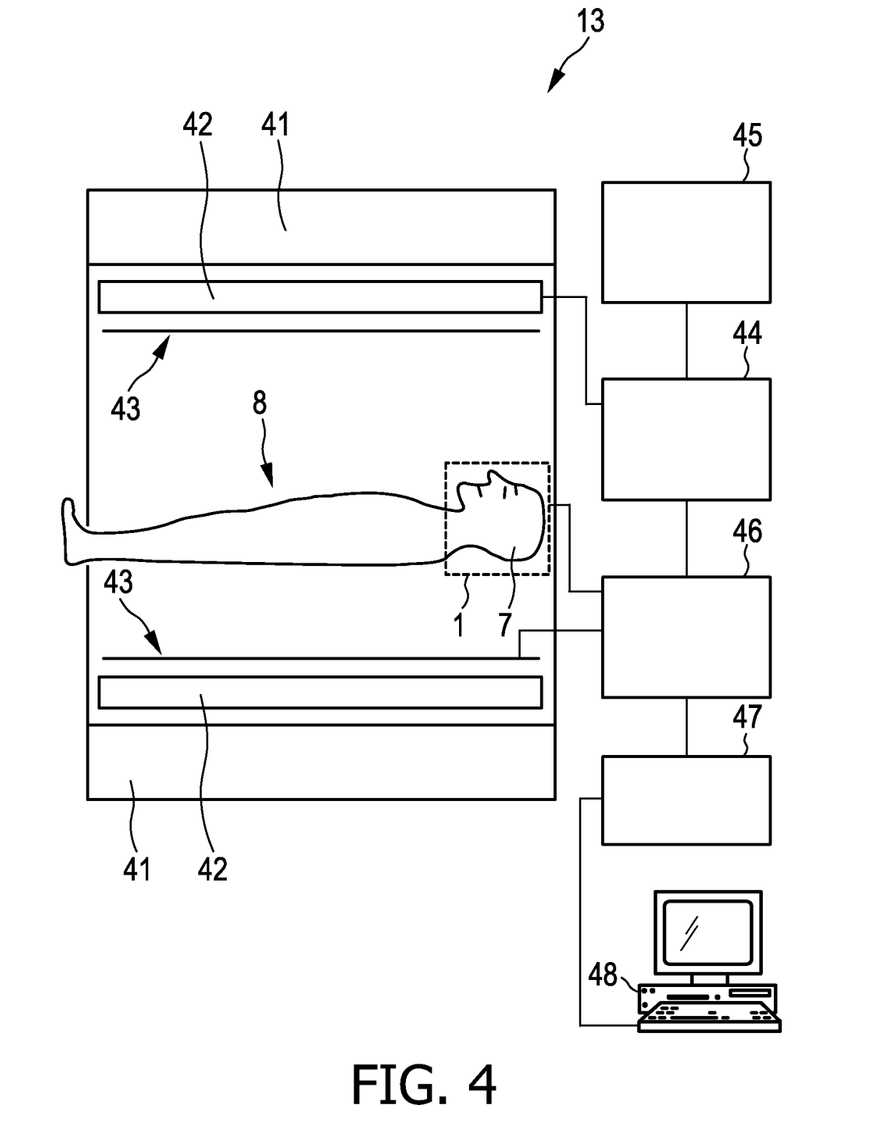
FIG. 4 shows schematically and exemplarily a magnetic resonance imaging system.

For generating the magnetic resonance image the person 8 with the head 7 located within the preparing apparatus 1 is arranged within a magnetic resonance imaging system which is schematically and exemplarily shown in FIG. 4.

The magnetic resonance imaging system 13 schematically and exemplarily shown in FIG. 4 is adapted to generate a magnetic resonance image of the head 7 of the person 8 by using magnetic resonance signals from the subject coil 3 of the preparing apparatus 1. The magnetic resonance imaging system 13 includes a main field magnet 41 for generating a B0 field in an imaging region comprising the head 7 of the person 8. Gradient coils 42 induce a gradient magnetic field across the B0 field, typically along three orthogonal axes. A whole body RF coil 43 transmits RF pulses to excite and manipulate resonance in the person 8, in particular, in the head 7, within the imaging region. Instead of using a whole body RF coil 43, a smaller RF coil can be used, which transmits RF pulses to excite and manipulate resonance substantially only in the head 7 of the person 8. Also the gradient coils for inducing a gradient magnetic field across the B0 field can be adapted to induce the gradient magnetic field in an imaging region covering substantially only the head 7 of the person 8, and also the main field magnet can be adapted to generate a B0 field substantially only in an imaging region being large enough for including the head of a person, but which is preferentially not larger. The subject coil 3 of the preparation apparatus 1, which is schematically indicated in FIG. 4 by a box with broken lines, receives the resonance signals from the head 7 of the person 8. Optionally, the subject coil 3 can also induce and/or manipulate resonance. A sequence controller 44 controls the RF and gradient coils 42 to implement a selected magnetic resonance imaging sequence. A sequence memory 45 stores these sequences. A magnetic resonance receiver 46 receives the magnetic resonance signals from the whole body RF coil 43 and the subject coil 3 of the preparing apparatus 1, and a reconstruction processor 47 reconstructs the received resonance signals into a magnetic resonance image of the head 7 of the person 8, which also shows the markers 9. A computer 48 with a user interface enables an operator to select imaging sequences to be performed, reconstruction operations, image formats and the like and displays the reconstructed image.

Figure 5:
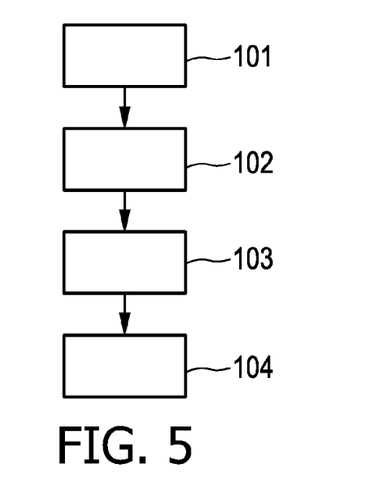
FIG. 5 shows a flowchart exemplarily illustrating a preparing method for preparing an influencing procedure for influencing a subject.

In the following an embodiment of a preparing method for preparing an influencing procedure for influencing a subject will exemplarily be described with reference to a flowchart shown in FIG. 5.

In step 101, the subject is positioned within the subject holding structure 4. Preferentially, the head 8 of a person 7 is positioned inside the RF head coil 3 and clamped in a fixed position within the RF head coil 3 using the clamping construction of the subject holding structure 4. Then, in step 102 a magnetic resonance image of the subject and of the marker is generated by using the RF head coil. In particular, the magnetic resonance imaging system 13 is used together with the preparing apparatus 1 to generate a three-dimensional magnetic resonance image that visualizes the person's anatomy with respect to the one or several markers 9 that are integrated in the RF head coil 3. Since in this embodiment a stereotactic procedure is described, the one or several markers can be regarded as stereotactic markers.

In step 103, an influence location, at which the subject should be influenced, is determined based on a provided influence location image region, which represents the influence location, within the generated magnetic resonance image, the generated magnetic resonance image, the position of the marker and the known spatial relationship between the instrument guide device and the subject coil, which will be present during influencing the subject, in particular, during the preferred stereotactic brain surgery procedure. This spatial relationship is known, because by using the above described preparation apparatus 1, after the instrument guide device has been attached to the subject coil, the spatial relationship between these devices is known. The influence location is preferentially an influence trajectory, in particular, a surgical trajectory. The influence location image region, in particular, an influence trajectory image region, can be provided by a person who is planning the influencing procedure based on the magnetic resonance image of the subject. In particular, a computer like the computer 48 shown in FIG. 4 with the user interface can be configured to allow a user to define an influence location image region, in particular, an influence trajectory image region, within the generated magnetic resonance image. Moreover, this computer or another calculation unit can be adapted to determine the influence location from the defined influence location image region. For example, the defined influence location image region can be translated into stereotactic coordinates that provide lateral, i.e. horizontal, and vertical positions and the angular orientation of the instrument holder, wherein the stereotactic coordinates define the determined influence location.

In step 104, the instrument guide device 5 is attached to the subject coil 2 by the attaching element 10 for allowing the instrument 6 to be guided by the instrument guide device 5 in accordance with the determined influence location, in order to influence the subject 8. In particular, the endplate 12 with the instrument holder 11 is fitted on the RF head coil 3 and the instrument holder is positioned, i.e. translated and/or rotated and/or tilted, according to the planned trajectory. Then, the influencing procedure, in particular, the brain surgery can be started and the instrument 6 can be moved and guided along the determined trajectory.

Although in the above described embodiments the one or several markers are arranged within the subject coil 3, the markers can also be provided on another part of the preparing apparatus. In an embodiment, the one or several markers being stereotactic markers which are visible in a magnetic resonance image are provided on the instrument guide device, in particular, on the instrument holder carrier. The instrument holder carrier is then attached to the subject coil before the magnetic resonance image is generated. In particular, the head of the person is positioned inside the RF head coil and clamped in fixed position in the RF head coil using the clamping construction. The instrument holder carrier is positioned in the RF head coil in a uniquely and mechanically robust way, and a three-dimensional magnetic resonance image is taken that visualises the person's anatomy and the one or several stereotactic markers. An influence location image region, in particular, a surgical trajectory image region, is provided in the magnetic resonance image and the influence location image region is translated into stereotactic coordinates that provides the lateral, i.e. horizontal, and vertical positions and the angular orientation of the instrument holder, in order to determine the influence location. The instrument holder is then positioned according to the determined influence location, in particular, according to the planned trajectory. The instrument is arranged within the instrument holder, or the instrument has already been arranged within the instrument holder, and the instrument is moved and guided in accordance with the determined influence location by the instrument guide device.

Figure 6:
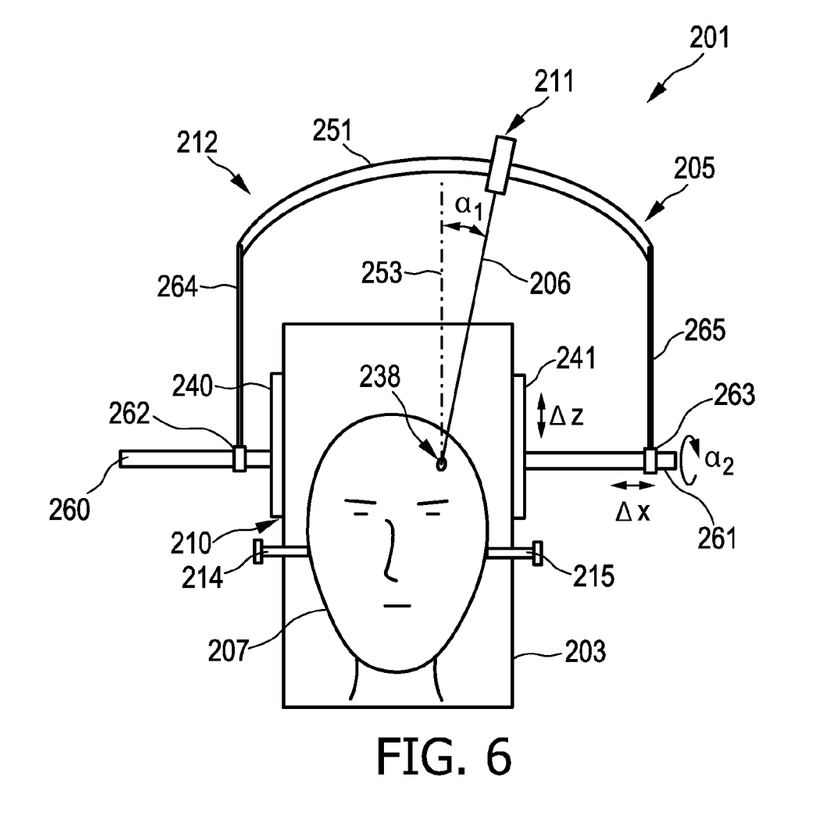
FIG. 6 shows schematically and exemplarily of a further embodiment of a preparing apparatus for preparing an influencing procedure for influencing a subject.

FIG. 6 shows schematically and exemplarily a further embodiment of a preparing apparatus for preparing an influencing procedure for influencing a subject. The preparing apparatus 201 comprises a subject coil 203 which is a RF head coil. The subject coil 203 is adapted to generate a magnetic resonance image of the subject 207 being a head of a person. The preparing apparatus 201 further comprises an instrument guide device 205 for guiding an instrument 206 for influencing the head 207. A marker, which is not shown in FIG. 6 for clarity reasons, is provided within the subject coil 203. The marker is visible in the generated magnetic resonance image and used for aligning purposes as described above. FIG. 6 further shows head clamping rods 214, 215 which protrude through corresponding openings in the subject coil 203, in order to fix the head 207 in a desired position. The instrument guide device 205 comprises an instrument holder 211 for holding the instrument 206 and an instrument holder carrier 212 for carrying the instrument holder 211. The instrument holder 211 and the instrument holder carrier 212 are adapted such that the instrument 206 can be guided through an opening 238 in the head 207 to a desired target location along a desired surgery trajectory.

The instrument holder carrier 212 comprises an arc element 251 along which the instrument holder 211 can be moved for arranging the instrument holder 211 at a desired angular position $\alpha_1$ with respect to a reference line 253 which is, in this embodiment, parallel to the central axis of the subject coil 203 and meets an opening 238 in the head 207, through which the instrument 206 is introduced. The instrument holder 211 can be fixed at a desired angular position $\alpha_1$ by using a fixation element like a fixation screw. The instrument holder carrier 212 further comprises rods 264, 265 to which the arc element 251 is attached. In particular, the arc element 251 is attached to first ends of the rods 264, 265 and opposing second ends of the rods 264, 265 are attached to rotational axes 260, 261 of the instrument holder carrier 212. The second ends of the rods 264, 265 are attached to the rotational axes 260, 261 such that the rods 264, 265 with the arc element 251 can be rotated around the rotational axes 260, 261 and translated along the rotational axes 260, 261, i.e. along the x direction. The instrument holder carrier 212 further comprises sliding elements 240, 241 being attached to the subject coil 203 via an attaching element 210. The rotational axes 260, 261 are attached to the sliding elements 240, 241 and the sliding elements 240, 241 are adapted such that the rotational axes 260, 261 can be moved in y, z directions which are perpendicular to the rotational axes 260, 261. The spatial relationship between the instrument guide device 205 and the subject coil 203, in particular, between the instrument holder 211 with the instrument 206 and the subject coil 203 is known while determining the target location and the corresponding surgery trajectory in stereotactic coordinates. The rotational position of the rods 264, 265 around the rotational axes 260, 261, which is indicated in FIG. 6 by $\alpha_2$, can be fixed by fixation elements like fixation screws and also the y, z position of the rotational axes 260, 261 on the sliding elements 240, 241 can be fixed by fixation elements like fixation screws. The second ends of the rods 264, 265 can comprise ring elements 262, 263, which receive the rotational axes 260, 261 for allowing the rods 264, 265 to be rotated around the rotational axes 260, 261.

Figure 7:
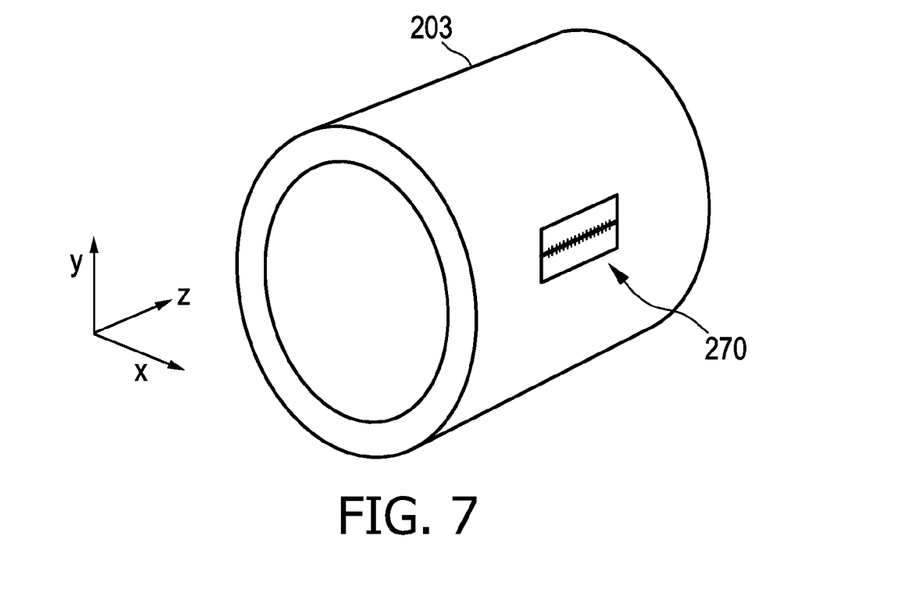
FIG. 7 shows schematically and exemplarily a subject coil with a rail element.
Figure 8:
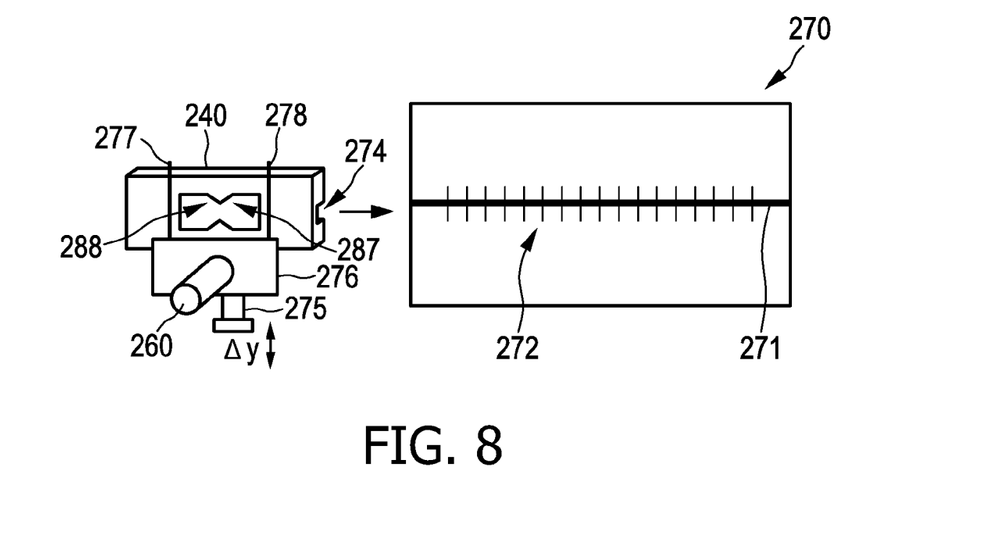
FIG. 8 shows schematically and exemplarily the rail element together with a sliding element for moving an instrument guide device with respect to the subject coil.

As schematically and exemplarily shown in FIG. 7, the subject coil 203 has a rail element 270 integrated in its side, for example, fabricated as one component into a housing of the subject coil 203. The rail element 270 is schematically and exemplarily shown in more detail in FIG. 8. The rail element 270 comprises a rail 271 and a metric scale 272, wherein the rail 271 is received by a groove 274 of the sliding element 240 for allowing the sliding element 240 to be translated with respect to the subject coil 203 in the z direction. The sliding element 240 can be fixed with respect to the rail element 270 by fixation elements like fixation screws, when a desired position has been set. A plate 276 with the rotational axis 260 is attached to the sliding element 240 such that the rotational axis 260 is moveable in the y direction with respect to the sliding element 240. In this embodiment, the sliding element 240 comprises two vertical slides 277, 278 on which the plate 276 can slide in the y direction. A rotational mechanism can be used for moving the plate 276 with the rotational axis 260 in the y direction with respect to the subject coil 203, wherein the y position can be modified by using an adjustment screw 275. In this embodiment, the rail 271 and the groove 274 form the attaching element 210. The sliding element 240 comprises an opening 288 with pointers 287 for indicating the z position on the metric scale 272.

The rail element can be a plate comprising the rail and the metric scale, which is provided on an outer surface of the subject coil, in particular, on an outer surface of a housing of the subject coil. However, the rail element can also comprise the rail and optionally the metric scale, without the plate, i.e. the rail can be provided directly on an outer surface of the subject coil, in particular, on an outer surface of the housing of the subject coil.

Figure 9:
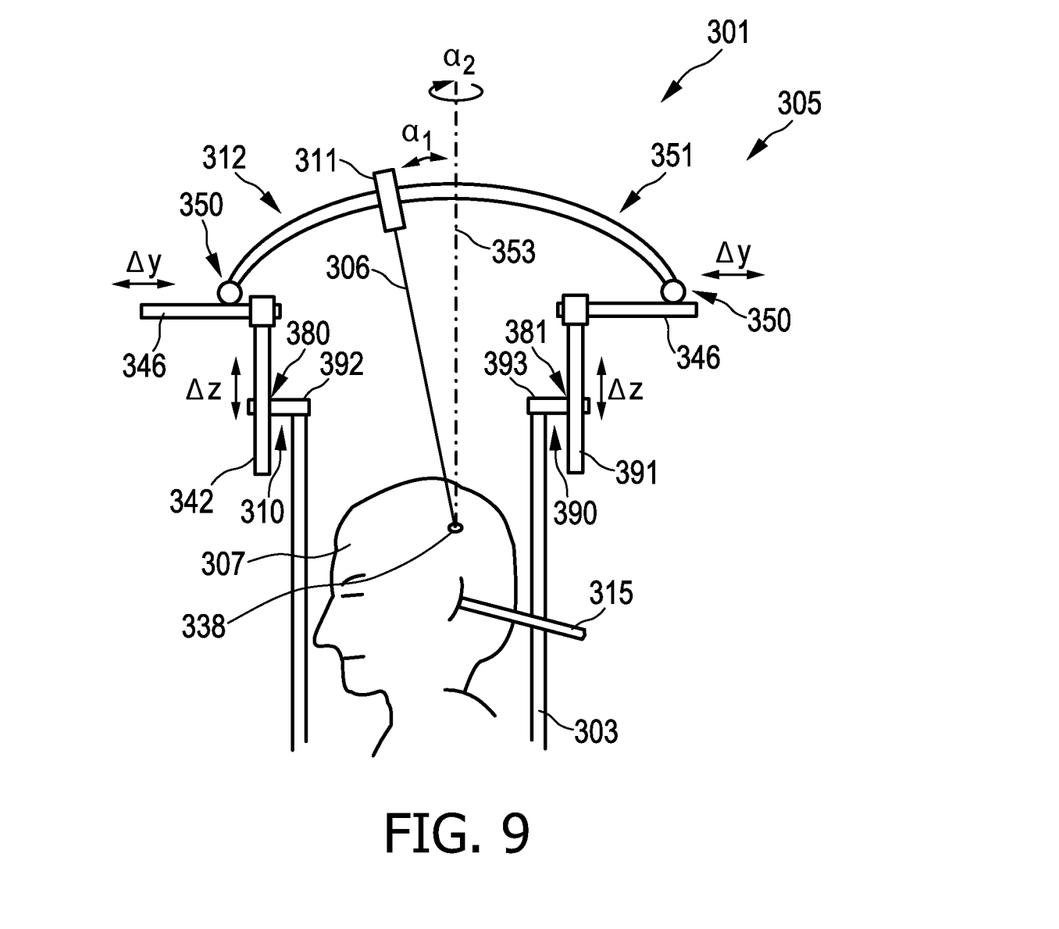
FIG. 9 shows schematically and exemplarily a further embodiment of a preparing apparatus for preparing an influencing procedure for influencing a subject.

FIG. 9 shows schematically and exemplary a further embodiment of a preparing apparatus for preparing an influencing procedure for influencing a subject. The preparing apparatus 301 comprises a subject coil 303 which is a RF head coil. The subject coil 303 is adapted to generate a magnetic resonance image of the subject 307 being a head of a person. The preparing apparatus 301 further comprises an instrument guide device 305 for guiding an instrument 306 for influencing the head 307. A marker, which is not shown in FIG. 9 for clarity reasons, is provided within the subject coil 303. The marker is visible in the generated magnetic resonance image and used for aligning purposes as described above. FIG. 9 shows further a head clamping rod 315 which protrudes through a corresponding opening in the subject coil 303, which is not shown in FIG. 9. FIG. 9 shows substantially a cross-sectional side view of the preparing apparatus 301. Thus, a second head clamping rod, which is used together with the first head clamping rod 315 for fixing the head 307, is not shown in FIG. 9.

The instrument guide device 305 comprises an instrument holder 311 for holding the instrument 306 and an instrument holder carrier 312 for carrying the instrument holder 311. The instrument holder 311 and the instrument holder carrier 312 are adapted such that the instrument 306 can be guided through an opening 338 in the head 307 to a desired target location along a desired surgery trajectory.

The instrument holder carrier 312 comprises an arc element 351 along which the instrument holder 311 is moveable for arranging the instrument holder 311 at a desired angular position $\alpha_1$ with respect to a rotational axis 353. A fixation element like a fixation screw is provided for fixing the instrument holder 311 at the desired angular position $\alpha_1$. The arc element 351 is supported on a circular rail 350 for allowing the arc element 351 to be rotated around the rotational axis 353. The circular rail 350 is attached to an xy stage 346 with a circular aperture and the xy stage 346 is movably attached to several, in particular, four, attachment pins 342, 391 surrounding the rotational axis 353. The xy stage 346 can translate the circular rail 350 with respect to the subject coil 303 in the x-direction and the y-direction, which are perpendicular to the rotational axis 353. Moreover, the attachment pins 342, 391 are attached to the subject coil 303 via attaching elements 310, 390. The attaching elements 310, 390 are adapted such that the xy stage 346 can be moved with respect to the subject coil 303 in the z-direction being parallel to the rotational axis 353. The attaching element 310, 390 are formed by hole elements 392, 393 with receiving holes 380, 381 for receiving the attachment pins 342, 391. Fixation elements like fixation screws are provided for fixing the attachment pins 342, 391 at a desired z position with respect to the hole elements 392, 393 and, thus, with respect to the subject coil 303. The attachment pins 342, 391 can comprise metric scales being indicative of the spatial relationship between the instrument guide device and the subject coil in the z direction. Metric scales can also be provided on the xy stage, wherein the spatial relationship between the instrument holder 311 and the subject coil 303 can be known from this metric scales. The preparing apparatus comprises fixation elements like fixation screws for fixing the instrument holder 311 at a desired position, i.e. for fixing the xy stage 346 with respect to the subject coil 303, the attachment pins 342, 391 with respect to the subject coil 303, the arc element 351 with respect to the xy stage 346 and the instrument holder 311 with respect to the arc element 351.

The circular rail 350 is adapted to allow the arc element 351 and, thus, the instrument holder 311 to be rotated around the rotational axis 353 over an angular range of 360 degree. This rotation is indicated in FIG. 9 by $\alpha_2$. The instrument guide device comprising the instrument holder 311, the arc element 351, the ring element 346 and the cylindrical element 342 can be rigidly attached to the subject coil 303 via the attaching element 310. The instrument guide device allows for a controllable translation in three perpendicular directions, a constructable rotation around the rotational axis 353, and a controllable movement of the instrument holder 311 along the arc element 351.

For precise delivery of instruments like needles, implants or other instruments in patient's brain, generally stereotactic neurosurgery is used. Commonly, a stereotactic procedure comprises following steps: Firstly, a stereotactic frame is attached to a patient's skull. Then, a preoperative three-dimensional image acquisition of a patient with the attached frame is performed by using, for example, a magnetic resonance imaging system or a computed tomography imaging system. Stereotactic markers or fiducials are identified in the acquired three-dimensional images and a stereotactic space is defined by performing a registration procedure. After that, targets and associated trajectories are defined, and the person is transferred to an operating room in which the surgery should be performed. An arc and instrument guide is attached to the frame and aligned to the defined trajectories, where upon the surgery starts. The main advantages of the stereotactic frame are the reliable mechanical guidance of the instrument along a pre-operatively determined trajectory and its long term proven use in surgical practice. Moreover, stereotactic surgery does not require large craniotomies, but only needs small burr holes to insert the instruments, thus limiting patient trauma. However, several disadvantages of using this known stereotactic frame are: a) the installation of the frame and registration to stereotactic space is time consuming, b) due to its size the device is invasive and cumbersome to use, c) the presence of the frame makes it difficult to fit in RF head coils, and d) essentially the surgical approach fully relies on the pre-operative images and is performed 'blindly' so that, for example, pre-operative changes in anatomy ('brain shift') or bending/deviations of instruments are unknown and cannot be accounted for. The preparing apparatus in accordance with the invention overcomes at least one of these disadvantages.

The preparing apparatus is preferentially adapted for a convenient attachment and registration of a stereotactic frame, wherein an instrument can be inserted into the subject, in particular, into the head of a person, within an MRI scanner and wherein the subject does preferentially not need to be moved in and out of the MR scanner. Moreover, in contrast to the above mentioned prior art, preferentially the instrument guide device does not need to be mounted to the subject, in particular, to the head of a person. This cumbersome and time consuming procedure is therefore preferentially not needed, if the preparing apparatus is used.

The one or several markers are, for example, bars filled with contrast fluid or active markers.

Although in the above described embodiments the preparing apparatus has been described as being adapted to prepare a surgery procedure for the head of a person, the preparing apparatus can also be adapted to prepare an influencing procedure for influencing another subject like another part of a person or of an animal or like a technical object.

Although in the above described embodiments, certain attaching elements have been described for attaching the instrument guide device and the subject coil to each other in a known spatial relationship, also other attaching elements can be used for generating another kind of attachment like screws or other attaching elements, as long as the attachment ensures a known spatial relationship between the subject coil and the instrument guide device.

Although a certain magnetic resonance imaging system and a corresponding procedure for generating magnetic resonance images have been described above with reference to FIG. 4, also other magnetic resonance imaging systems and corresponding procedures for generating magnetic resonance images can be used, as long as the generated magnetic resonance images show the subject and at least one marker.

The subject comprises preferentially a subject coil housing in which a subject coil wire is housed. The attaching element, in particular, parts of the attaching element like a receiving element or a rail element can be provided on the subject coil housing of the subject coil.

After the instrument guide has been attached to the subject coil, the spatial relationship between the instrument guide device and the subject coil, in particular, between the instrument holder and the subject coil and, thus, between the instrument and the subject coil is known. In an embodiment, the preparing apparatus comprises metric scales being indicative of the spatial relationship.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention relates to a preparing apparatus for preparing an influencing procedure for influencing a subject. The preparing apparatus comprises a subject coil for generating a magnetic resonance image of the subject, an instrument guide device for guiding an instrument for influencing the subject, a marker being visible in the magnetic resonance image, and an attaching element for attaching the instrument guide device to the subject coil in a known spatial relationship. Since the spatial relationship between the instrument guide device and the subject coil is known, if they are attached to each other, a time consuming registration procedure for registering an influence trajectory, which has been planned based on the magnetic resonance image, and the instrument guide device can be avoided.

The invention claimed is:

1. A preparing apparatus for preparing an influencing procedure for influencing a subject, the preparing apparatus comprising:
   a subject coil for acquiring magnetic resonance signals for generating a magnetic resonance image of the subject,
   an instrument guide device for guiding an instrument for influencing the subject,
   a marker being visible in the magnetic resonance image,
   an attaching element for attaching the instrument guide device to the subject coil,
   wherein the attaching element is adapted to attach the instrument guide device to the subject coil in a known spatial relationship, wherein the marker is attached to the subject coil and arranged within the subject coil.

2. The preparing apparatus as defined in claim 1, wherein the instrument guide device comprises an instrument holder for holding the instrument and an instrument holder carrier for carrying the instrument holder, wherein the attaching element is adapted to attach the subject coil and the instrument holder carrier to each other such that the instrument guide device and the subject coil are in a known spatial relationship.

3. The preparing apparatus as defined in claim 2, wherein the instrument holder and the instrument holder carrier are adapted to allow the instrument holder to be moved with respect to the instrument holder carrier for moving the instrument with respect to the subject coil.

4. The preparing apparatus as defined in claim 1, wherein the preparing apparatus further comprises a subject holding structure for holding the subject.

5. The preparing apparatus as defined in claim 4, wherein the subject coil is arranged within the subject holding structure.

6. The preparing apparatus as defined in claim 4, wherein the subject holding structure comprises more deformable regions and less deformable regions, wherein the subject coil is attached to the subject holding structure at the less deformable regions of the subject holding structure.

7. A magnetic resonance imaging system for imaging a subject, wherein the magnetic resonance imaging system comprises the subject coil with the marker of the preparing apparatus as defined in claim 1, wherein the magnetic resonance imaging system is adapted to generate a magnetic resonance image of the subject by using magnetic resonance signals from the subject coil.

8. A preparing method for preparing an influencing procedure for influencing a subject, wherein the preparing method is adapted to use the preparing apparatus as defined in claim 1 and comprises:

generating a magnetic resonance image of the subject and of the marker by using the subject coil, determining an influence location, at which the subject should be influenced, based on a provided influence location image region, which represents the influence location, within the generated magnetic resonance image, the generated magnetic resonance image, the position of the marker and the known spatial relationship between the instrument guide device and the subject coil, which will be present during influencing the subject, attaching the instrument guide device to the subject coil by the attaching element for guiding the instrument by the instrument guide device in accordance with the determined influence location for influencing the subject.

* * * * *